United States Patent [19]
Morales

[11] Patent Number: 5,972,016
[45] Date of Patent: Oct. 26, 1999

[54] STENT CRIMPING DEVICE AND METHOD OF USE

[75] Inventor: Stephen A. Morales, Mountain View, Calif.

[73] Assignee: Advanced Cardiovascular Systems, Inc., Santa Clara, Calif.

[21] Appl. No.: 08/837,771

[22] Filed: Apr. 22, 1997

[51] Int. Cl.⁶ .................................................. A61M 29/00
[52] U.S. Cl. .............................................. 606/198; 606/1
[58] Field of Search ........................... 606/1, 108, 191, 606/194, 195, 198, 200; 623/1, 12; 128/898, 899; 29/234, 235, 282, 283

[56] References Cited

U.S. PATENT DOCUMENTS

| | | |
|---|---|---|
| 4,468,224 | 8/1984 | Enzmann et al. . |
| 4,576,142 | 3/1986 | Schiff . |
| 4,644,936 | 2/1987 | Schiff . |
| 4,681,092 | 7/1987 | Cho et al. . |
| 4,697,573 | 10/1987 | Schiff . |
| 4,901,707 | 2/1990 | Schiff . |
| 4,907,336 | 3/1990 | Gianturco . |
| 5,132,066 | 7/1992 | Charlesworth et al. . |
| 5,133,732 | 7/1992 | Wiktor . |
| 5,183,085 | 2/1993 | Timmermans . |
| 5,195,539 | 3/1993 | Dyrud et al. . |
| 5,546,646 | 8/1996 | Williams et al. . |
| 5,626,604 | 5/1997 | Cottone, Jr. . |
| 5,630,830 | 5/1997 | Verbeek . |
| 5,653,691 | 8/1997 | Rupp et al. . |
| 5,672,169 | 9/1997 | Verbeek . |
| 5,738,674 | 4/1998 | Williams et al. . |
| 5,746,764 | 5/1998 | Green et al. . |
| 5,783,227 | 7/1998 | Dunham . |
| 5,785,715 | 7/1998 | Schatz . |

FOREIGN PATENT DOCUMENTS

| | | |
|---|---|---|
| 0 630 623 | 12/1994 | European Pat. Off. . |
| 0 826 346 | 3/1998 | European Pat. Off. . |

OTHER PUBLICATIONS

*The eXTraordinary Stent*, C.R. Bard Brochure (Undated).

*Primary Examiner*—William Lewis
*Attorney, Agent, or Firm*—Fulwider Patton Lee & Utecht, LLP

[57] ABSTRACT

A device and method for enabling substantially uniform and tight crimping of an intravascular stent onto a balloon catheter assembly. The device has a base portion having an intermediate portion and pivoting arm portions attached thereto. A loop portion is attached at its end portions to the pivoting handle portions. The loop portion has a compressible and generally cylindrical opening which is substantially uniformly compressible radially inwardly upon pivoting the arm portions downwardly from the intermediate portion. This substantially uniformly and tightly crimps the stent onto the catheter portion which is inserted therein.

10 Claims, 5 Drawing Sheets

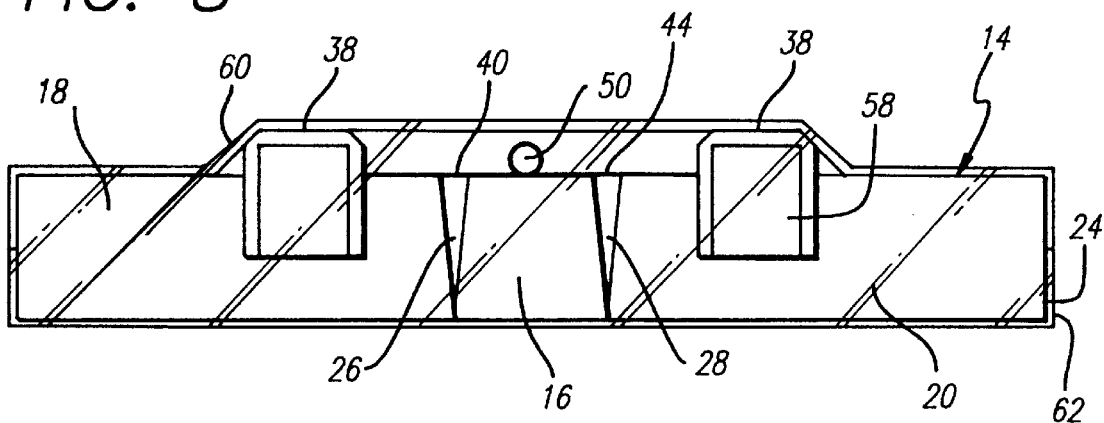
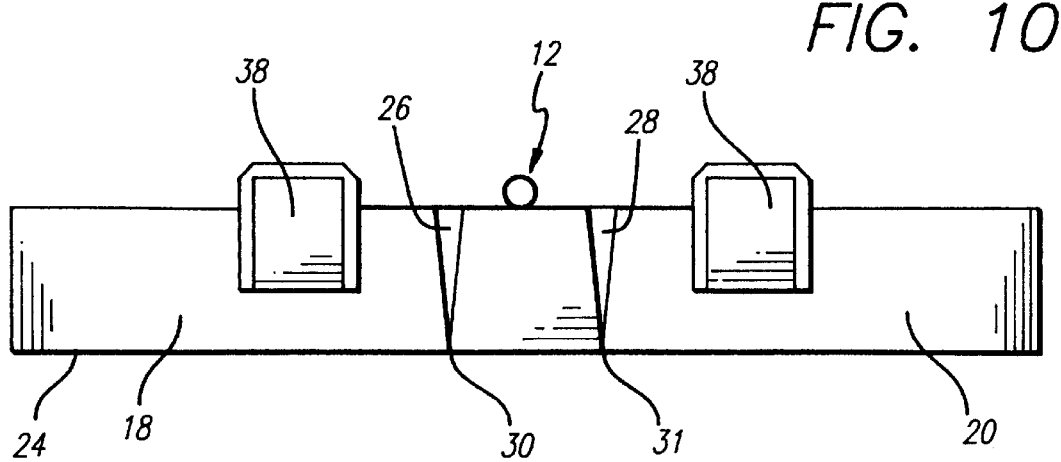
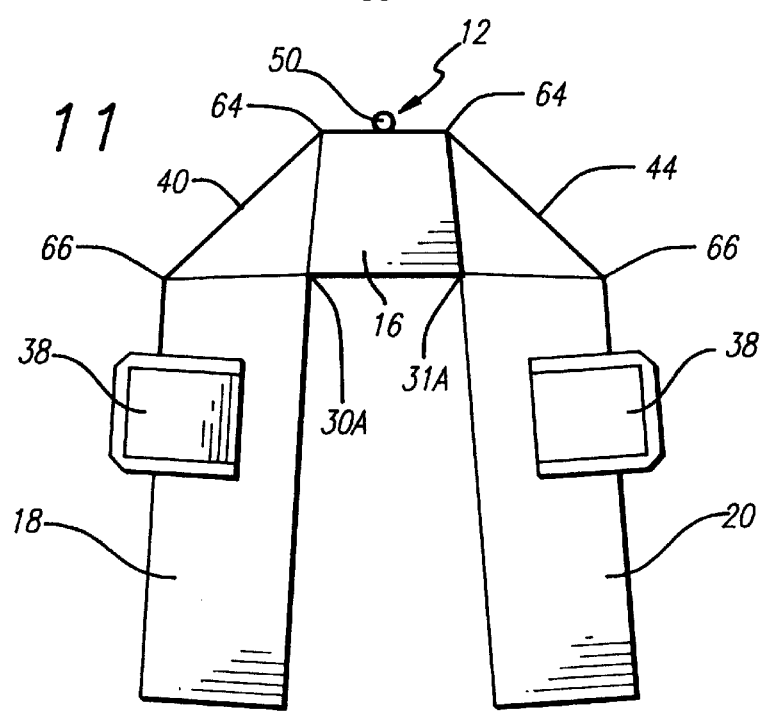

STENT CRIMPING DEVICE AND METHOD OF USE

BACKGROUND OF THE INVENTION

1. Field of the Invention

This invention relates to a stent crimping device and method of use of the type that will enable an end user to firmly crimp a stent onto the distal end of a catheter assembly.

2. Description of the Related Art

In a typical percutaneous transluminal coronary angioplasty (PTCA) procedure, for compressing lesion plaque against the artery wall to dilate the arterial lumen, a guiding catheter is percutaneously introduced into the cardiovascular system of a patient through the brachial or femoral arteries and advanced through the vasculature until the distal end is in the ostium. A guidewire and a dilatation catheter having a balloon on the distal end are introduced through the guiding catheter with the guidewire sliding within the dilatation catheter. The guidewire is first advanced out of the guiding catheter into the patient's coronary vasculature, and the dilatation catheter is advanced over the previously advanced guidewire until the dilatation balloon is properly positioned across the lesion. Once in position across the lesion, a flexible, expandable, preformed balloon is inflated to a predetermined size at relatively high pressures to radially compress the atherosclerotic plaque of the lesion against the inside of the artery wall and thereby dilate the lumen of the artery. The balloon is then deflated to a small profile, so that the dilatation catheter can be withdrawn from the patient's vasculature and blood flow resumed through the dilated artery. While this procedure is typical, it is not the only method used in angioplasty. Further, other methods are well known in opening a stenosed artery such as atherectomy devices, plaque dissolving drugs, and the like.

In angioplasty procedures of the kind referenced above, there may be restenosis of the artery, which may require another angioplasty procedure, a surgical bypass operation, or some method of repairing or strengthening the area. To reduce the chance of restenosis and strengthen the area, a physician can implant an intravascular prosthesis for maintaining vascular patency, typically called a stent. A stent is a device used to hold tissue in place or to provide a support for a graft or tissue joined together while healing is taking place. A variety of devices are known in the art for use as stents, including coiled wires and wire mesh sleeves, in a variety of patterns, that are able to be crimped onto a balloon catheter, and expanded after being positioned intraluminally on the balloon catheter, and that retain their expanded form. Typically the stent is mounted and crimped onto the balloon portion of the catheter, and advanced to a location inside the artery at the lesion. The stent is then expanded to a larger diameter, by the balloon portion of the catheter, to implant the stent in the artery at the lesion. Examples of stents and delivery catheters of the type described herein are disclosed in more detail in U.S. Pat. No. 5,102,417 (Palmaz); U.S. Pat. No. 5,514,154 (Lau et al.); and U.S. Pat. No. 5,56,295 (Lam), incorporated herein by reference.

However, if the stent is not tightly crimped onto the catheter balloon portion, when the catheter is advanced in the patient's vasculature the stent may slide off the catheter balloon portion in the coronary artery prior to expansion, and may block the flow of blood, requiring procedures to remove the stent.

In procedures where the stent is placed over the balloon portion of the catheter, the stent must be crimped onto the balloon portion to prevent the stent from sliding off the catheter when the catheter is advanced in the patient's vasculature. In the past, the crimping procedure was often done by hand, which may result in uneven force being applied, resulting in non-uniform crimps. In addition, it was difficult to judge when a uniform and reliable crimp had been applied or if the stent had damaged the balloon. Though some tools, such as ordinary pliers, have been used to crimp the stent, these tools have not been entirely adequate in achieving a uniform crimp.

There accordingly remains a need for improved tools and methods to secure stents on the balloon portions of catheters.

SUMMARY OF THE INVENTION

This invention is directed to a vascular prosthesis crimping device which enables substantially uniform and tight crimping of a stent onto a catheter balloon portion, to better secure the stent onto the catheter for delivery of the stent through the patient's vasculature, while at the same time permitting uniform expansion of the stent in a patient's artery, vein, duct, or other vessel or lumen. The present invention attempts to solve several problems associated with crimping stents onto balloon catheters.

In an exemplary embodiment of the present invention, the stent crimping device includes a radially compressible and resiliently radially expandable cylindrical loop portion having opposed side edges extending from the loop portion. These side edges are secured to pivoting arm portions of the device. The inner diameter of the loop portion is compressible radially inwardly by the user moving the pivoting arm portions downwardly to substantially uniformly and tightly crimp the stent onto the balloon catheter assembly inserted within the loop portion. The loop portion is returned to its expanded state upon bringing the pivoting arm portions back to their un-pivoted position thereby allowing the stent crimped onto the catheter balloon to be withdrawn by the user.

The device enables the stent to be crimped onto the distal end of a balloon catheter substantially uniformly and tightly, reducing the risk that the stent may inadvertently shift or slide off the catheter balloon portion. Further, it is easy to use in performing the stent crimping procedure. The device, due to its simplicity, low manufacturing and assembly cost, and adaptability to compressing stents of different length and diameter, is particularly well suited for use in compressing stents onto balloon catheters of different manufacturers, and ideally suited as a one-time use disposable device, thereby eliminating the need for sterilization of the device between uses.

These and other advantages of the invention will become more apparent from the following detailed description thereof when taken in conjunction with the accompanying drawings.

BRIEF DESCRIPTION OF THE DRAWINGS

FIG. 8 is a side view of the device packaged to maintain its loop portion, in its open position, wherein the loop portion cannot be radially compressed.

FIG. 10 is a side view of the device with packaging removed, in its open position prior to radial compression of the loop portion.

FIG. 11 is a side view of the device with the arm portions of the main body portion pivoted downwardly away from the intermediate portion to cause the loop portion to constrict in diameter, to thereby crimp a stent around the balloon portion of the catheter which has been positioned within the loop portion.

DETAILED DESCRIPTION OF THE PREFERRED EMBODIMENTS

Figure 1:
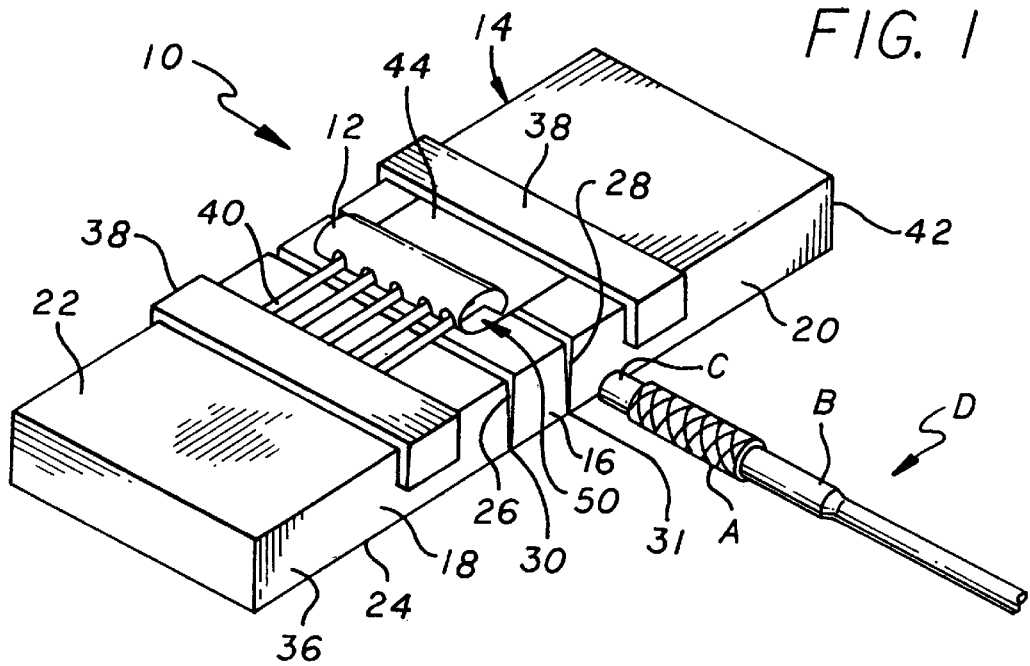
FIG. 1 is a perspective view of an exemplary embodiment of the present invention, in its open position, in which the loop portion of the device is fully expanded for receipt of a stent to be compressed onto a balloon catheter.

The invention comprises a tool 10 and method for use in uniformly and tightly crimping an intravascular stent A onto the collapsed balloon portion B adjacent the distal end C of a balloon catheter assembly D. In the exemplary embodiment of device 10, as shown in FIGS. 1 and 10, tool 10 is adapted to be held in the hand of the user. The user will insert stent A, previously placed over the collapsed balloon B, into the loop portion 12 to enable stent A and catheter D to be supported in tool 10, and to enable the user to apply compressive force to tool 10 to substantially uniformly and tightly crimp stent A onto collapsed balloon B of catheter D.

Figure 2:
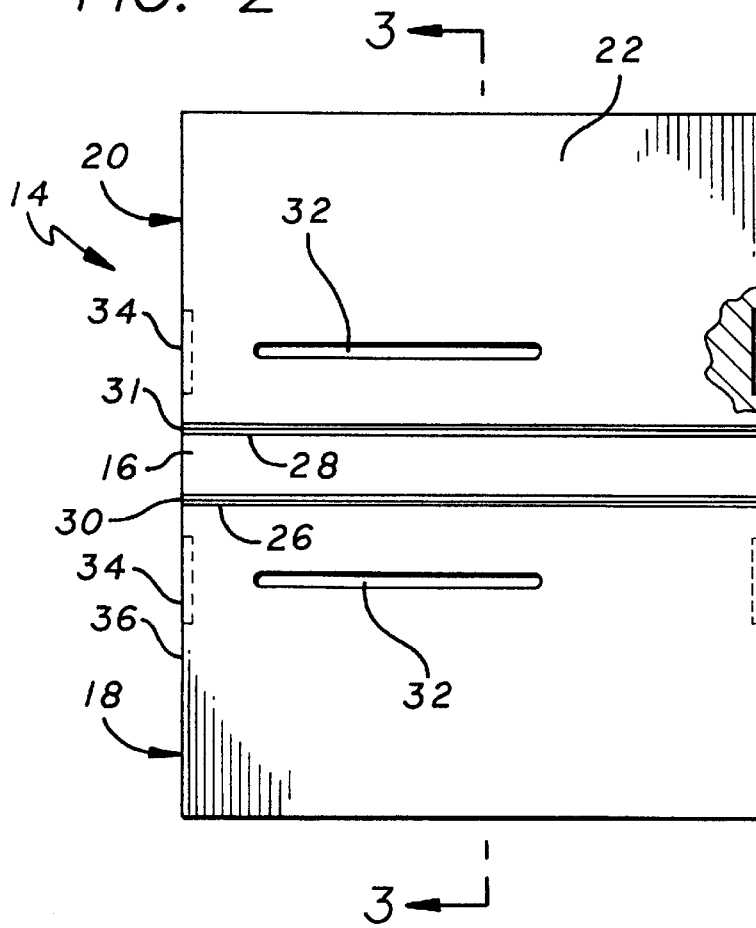
FIG. 2 is a top plan view of the main body portion of the present invention as shown in FIG. 1.
Figure 3:
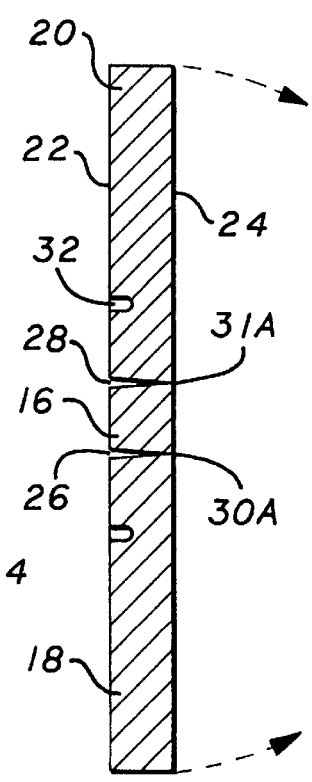
FIG. 3 is a cross-sectional view through view lines 3—3 of FIG. 2.

Tool 10 includes a loop portion 12 affixed to a base portion 14 wherein the circumference of loop portion 12 is variable. Base portion 14 has an intermediate portion 16 which is pivotally connected to two pivoting arm portions 18 and 20. Base portion 14 has a top surface 22 on which loop 12 rests. Base portion 14 ideally comprises a single flat piece of material, such as plastic, with a pair of parallel longitudinal V-shaped slits 26 and 28 extending from the top surface 22 almost all the way to the bottom surface 24, the slits 26 and 28 terminating in lower parallel edges 30, 31, each forming hinges 30A and 31A to permit pivoting arm portions 18 and 20 to swing downwardly away from intermediate portion 16. When base portion 14 is formed from a single piece of plastic (or metal), then hinges 30A and 30B can be said to be living hinges formed in base portion 14. Alternatively, base portion 14 and pivoting arm portions 18,20 can be formed separately and connected by hinges 30A,30B which can be added and include conventional hinge designs. Referring to FIGS. 2 and 3, pivoting arm portions 18 and 20 have first engagement means, for example slots 32, formed in their top surface 22. Recesses 34 are formed on side edges 36 of pivoting arms 18 and 20, as best shown in FIG. 2. Clip portions 38 are used to secure loop portion 12 to base portion 10.

Figure 4:
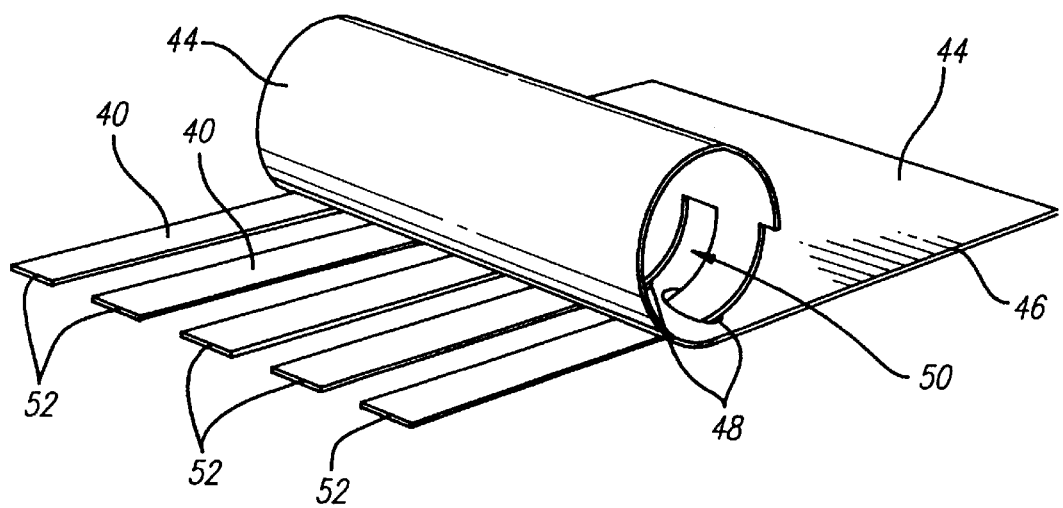
FIG. 4 is a perspective side view of a preferred embodiment of the loop portion of the device in its threaded orientation.
Figure 5:
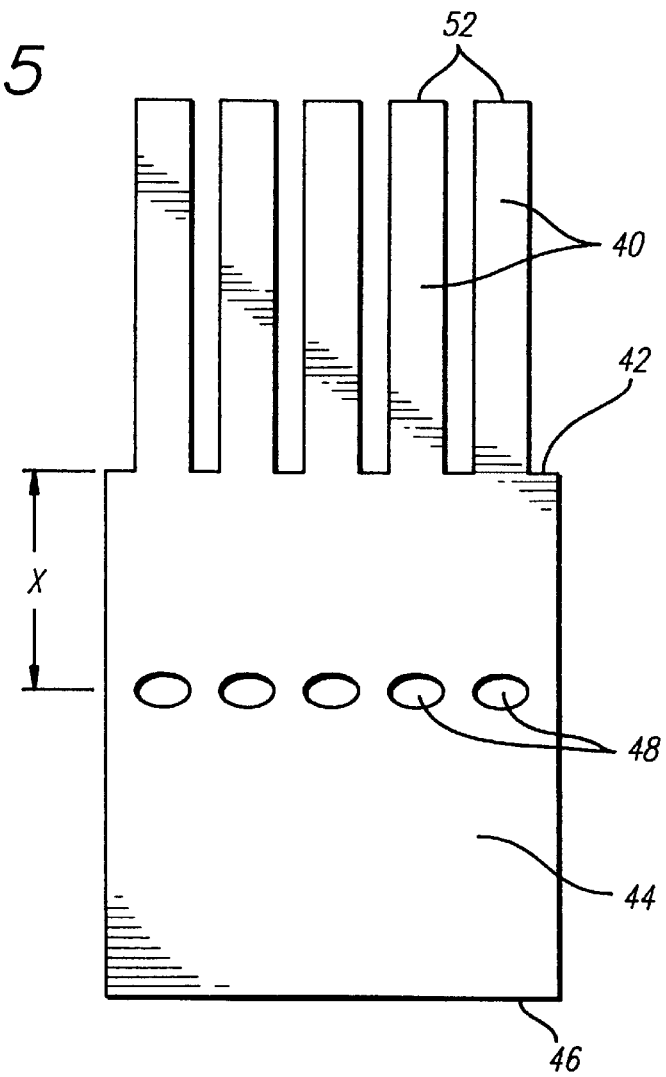
FIG. 5 is a plan view of the sheet of material forming the loop portion prior to being threaded.

Referring to FIGS. 4 and 5, a preferred embodiment of loop portion 12 is shown in greater detail. Loop portion 12 comprises a sheet of thin and flexible yet strong material, such as the polyester film Mylar® and has a plurality of elongate straps 40 extending from a first end 42 of sheet 44 and extending opposite a second end 46 of sheet 44. Other known flexible materials can be used. Apertures 48 formed in sheet 44 are adapted to receive straps 40 when threaded therethrough, as shown in FIGS. 1 and 4, thereby forming a generally cylindrical opening 50 for receiving stent A placed on the distal end C of balloon catheter B. Straps 40 have terminal end regions 52. By pulling terminal end regions 52 of straps 40 and the second end 46 away from each other, the generally cylindrical opening 50 will constrict in size, from its larger size shown in FIGS. 1, 4, 8 and 9, to the constricted size shown in FIG. 10.

As seen in FIG. 5, the distance X between aperture 48 and first end 42 of straps 40 will determine the smallest diameter of loop portion 12. Those skilled in the art will appreciate that distance X can be varied depending upon the diameter of the stent and balloon, and ultimately the crimped diameter of the stent on the balloon. The thickness of the polyester film forming loop portion 12 is an important consideration in the ability of the loop to rebound open after the stent is crimped. Thus, the polymer film preferably has a thickness in the range of 0.002 to 0.008 inches. With this range of thickness for the polymer film of loop 12, it is flexible and durable, and will readily rebound open to form open loop 12 after the stent is crimped on the balloon and removed from within loop 12.

In a preferred embodiment of the invention, straps 40 can be about 5 mm wide (0.2 inches), with about 2.5 mm (0.1 inches) of open space between the straps 40. The entire length of sheet 44, the length of straps 40 and spacing of apertures 48 from first end 42, can be chosen depending on the size of loop portion 12 desired. In lieu of a sheet of Mylar® or other sheet material, a plurality of wires or cords can be utilized to form loop portion 12.

Figure 6:
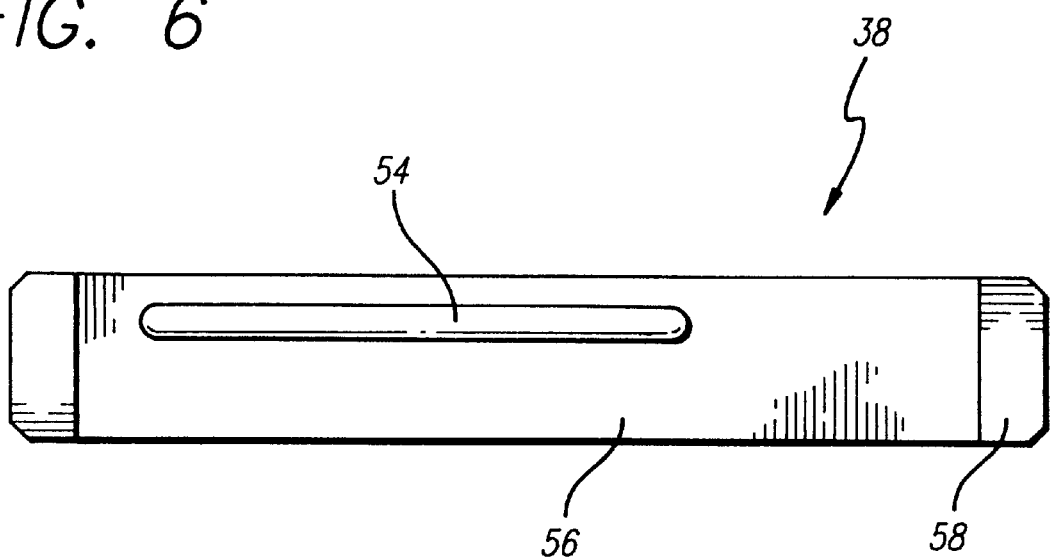
FIG. 6 is a bottom view of securing clips of the device used to secure the loop portion to the main body portion.
Figure 7:
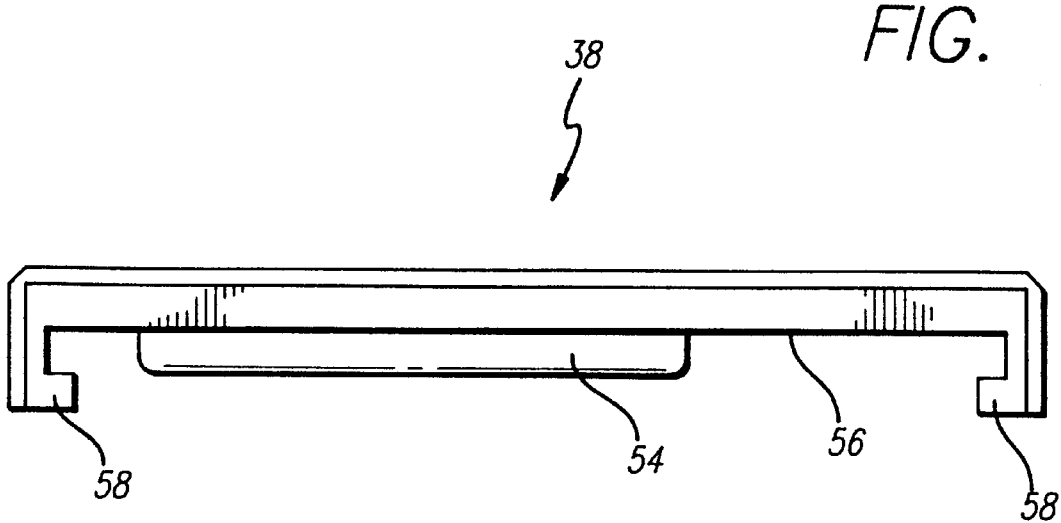
FIG. 7 is a side view of the securing clips of the device of FIG. 6.

The end regions 52 and end 46 of loop portion 12 are secured to tool 10 for radially compressible and expandable movement as follows. Referring to FIGS. 2, 3, 6 and 7, slots 32 formed on upper surface 22 of pivoting arm portions 18 and 20 (FIGS. 2 and 3), are adapted to receive a complementary engagement portion, for example, bar portion 54 extending from a bottom surface 56 of clip portion 38. Clip ends 58 are formed on ends of clip portions 38 (FIGS. 6 and 7). After placing loop portion 12 on top surface 22 of intermediate portion 16 and extending terminal end regions 52 of finger portions 40 and second end 46 over slots 32 in pivoting arms 18 and 20, clip portions 38 are snapped onto pivoting arms 18 and 29 with complementary bar portions 54 fitting into slots 32 and clip ends 58 fitting into recesses 34. This secures terminal end regions 52 of elongate straps 40 and second end 46 of loop portion, yet allows the portion of loop portion defining generally cylindrical opening 50 to ride on intermediate portion 16. In addition to this mechanical affixation, adhesives and other means can be utilized to secure elongate straps 40 and 52 of loop portion 12 to base portion 14. An advantage of device 10 is that its components, viz., base portion 14, loop portion 12 and clip portions 38 are all relatively low in cost, and base portion 14 and clip portions 38 will accommodate a loop portion 12 of desired diameter and length, to accept a balloon catheter D and stent A of desired diameter and length.

Figure 9:
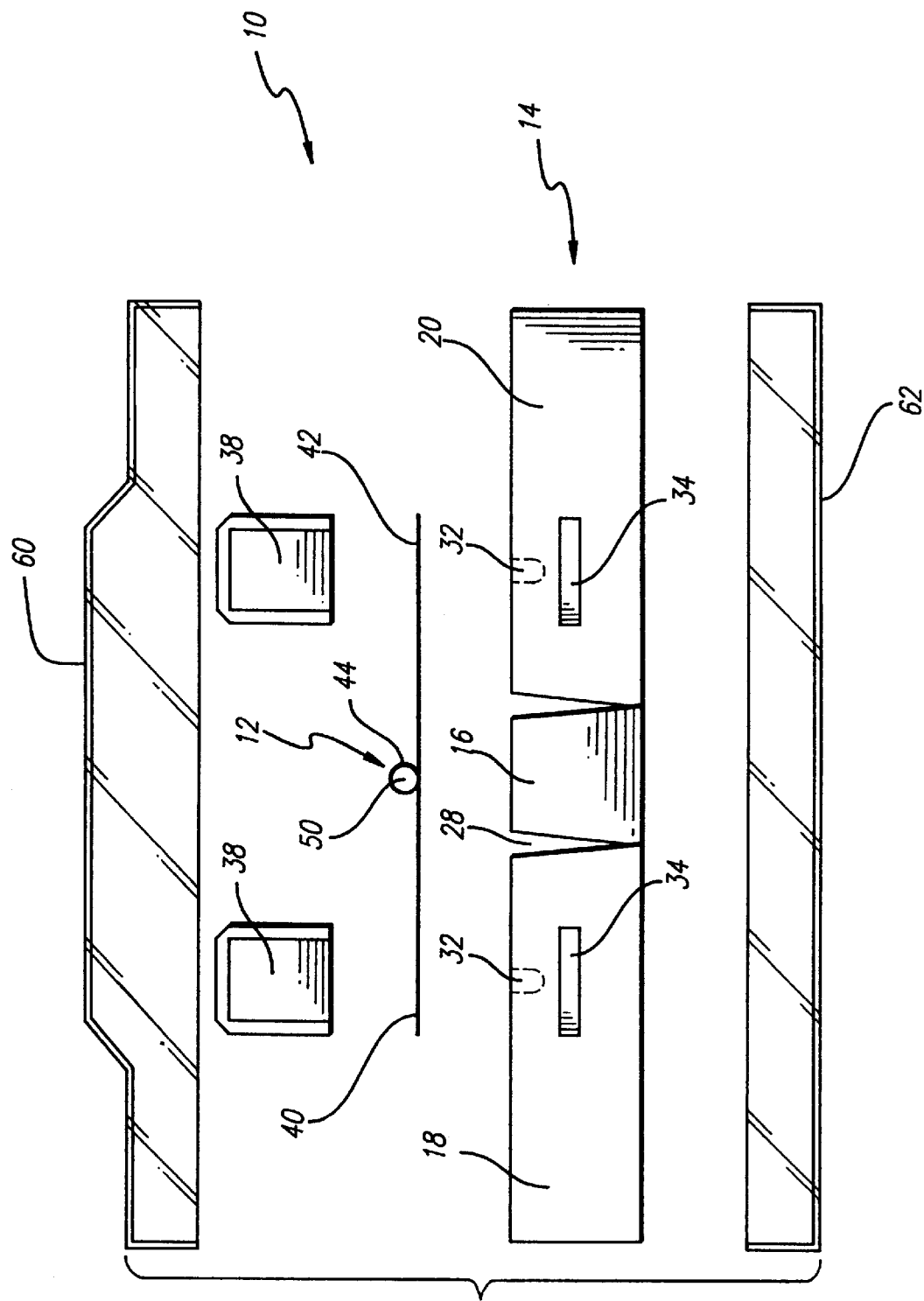
FIG. 9 is an exploded side view of the parts of the device and its packaging prior to being assembled.

Referring to FIG. 8, upper surface 22 of base portion 14, clip portions 38, and loop portion 12 are covered with protective layer 60 which cushions upper surface 22 and loop portion 12, and prevents loop portion 12 from being inadvertently crushed. The protective layer 60 can comprise bubble pack material, a vacuum formed plastic cover, or other known materials. To prevent arms 18 and 20 and intermediate portion 16 of base portion 14 from being pivoted, a rigid support sheet 62 is preferably positioned on lower surface 24 of base portion 14. Other means can be provided to protect the device 10 such as a case or box to surround the device in a sterile environment. FIG. 9 is an exploded side view of the device 10 and its packaging. FIG. 10 shows device 10 after being removed from its packaging 60 and 62 and ready for use.

Referring to FIGS. 1 and 11, in a preferred method of operation, a user will load stent A onto a deflated (unused) balloon portion B of balloon catheter assembly D. Catheter balloon portion B are then inserted in stent A so that stent A overlies balloon portion B. To enable stent A to be crimped onto catheter balloon portion B, stent A and catheter balloon portion B is inserted within loop portion 12 and supported in the middle of loop portion 12 which is carried on intermediate portion 16 of base portion 14. At this point, stent A is not fixed onto catheter assembly D, because stent A has not been compressed.

To crimp stent A onto catheter balloon portion B, the user of tool 10 simultaneously swings arm portions 18 and 20 downwardly together relative to intermediate portion 16. Swinging arm portions 18 and 20 downwardly causes ends 52 of straps 40 and sheet portion 46 to be pulled in opposite directions in a noose-like manner. Elongate straps 40 and sheet portion 44 on the sides of loop portion 12 will extend between opposite edges 64 and 66 of intermediate portion 16 and pivoting arm portions (18 and 20), respectively. As swinging arm portions 18 and 20 are swung down from intermediate portion 16, generally cylindrical opening 50 in loop portion 14 will constrict to a smaller inner diameter, compressing stent A radially inwardly and tightly onto catheter balloon portion B at a substantially uniform rate.

If further crimping of stent A onto catheter balloon portion B is desired, the user may rotate the crimped stent A and catheter balloon portion B and/or move them forward or backward in loop portion 12, and repeat the crimping procedure until stent A is as tightly crimped on catheter balloon portion B as desired.

After stent A has been crimped onto catheter balloon portion B, the user will swing arm portions 18 and 20 back up, thereby enlarging the generally cylindrical opening 50, enabling removal of crimped stent A and catheter balloon portion B from generally cylindrical opening 50. Balloon catheter assembly D, with stent A crimped thereon, may then be inserted into the body of the patient for deployment of stent A therein, (not shown).

As will be appreciated by those skilled in the art, the stent crimping assembly of the present invention is designed both for single use applications in a cath lab for use by a physician, or for multiple use applications in a sterile environment in a high volume manufacturing facility. Referring to the latter, where sterile conditions exist, the stent crimping assembly can be used to repeatedly crimp stents on balloons until the polyester film wears out and has to be replaced. Thus, repeated uses are contemplated for controlled sterile environments, however, single use applications are required when used by cath lab personnel.

While in the preferred embodiments the stent described herein is intended to be an intraluminal vascular prosthesis for use within a blood vessel, and the balloon delivery catheter is of the kind used in therapeutic coronary angioplasty or similar thereto, it will be appreciated by those skilled in the art that modifications may be made to the present invention to allow the present invention to be used to load any type of prosthesis. The present invention is not limited to stents that are deployed in a patient's vasculature but has wide applications to loading any type of graft, prosthesis, liner or similar structure. Furthermore, the stent may be delivered not only into coronary arteries but into any body lumen. Other modifications can be made to the present invention by those skilled in the art without departing from the scope thereof.

What is claimed is:

1. A device for substantially uniform and tight crimping of an intravascular stent loaded onto a portion of a catheter of a catheter assembly by a user, so as to enable the user to apply compressive force thereto to substantially uniformly and tightly crimp the stent onto the catheter assembly, the crimping device comprising:

a base portion having an intermediate portion and pivoting arm portions pivotally attached to the intermediate portion; and a loop portion attached to the pivoting arm portions, for use in supporting the stent and catheter portion, the loop portion having a compressible and generally cylindrical opening portion which is substantially uniformly compressible radially inwardly upon the application of force to said pivoting arm portions to substantially uniformly and tightly crimp the stent onto the catheter portion.

2. The device as in claim 1, wherein the loop portion of the device comprises a sheet of flexible material having end portions, the end portions including a plurality of elongate straps extending from a first side edge of the sheet and a second side edge of the sheet, the sheet having apertures formed therethrough, wherein the elongate straps are threaded through the apertures formed in the sheet to form a generally cylindrical opening portion, the opening being adapted to constrict when the elongate straps and the second side edge of the sheet are pulled in opposite directions.

3. The device as in claim 2, further comprising a pair of clips for affixing portions of the elongate straps and a portion of the second side edge of the loop portion to the pivoting arm portions, with the generally cylindrical opening portion placed on the intermediate portion.

4. The device as in claim 3, wherein each pivoting arm portion has an engagement portion formed thereon and wherein the clips have complementary engagement portions adapted for engagement with the pivoting arm engagement portions to retain end portions of the loop portion positioned thereon.

5. The device as in claim 4, wherein the engagement portion on the pivoting arm portions comprise slots formed on an upper surface and side edges thereof, the complementary engagement portion of the clips comprise a bar on an underside of each of the clips and a plurality of clip ends adapted to firmly attach to the slots on side edges of the pivoting arm portions.

6. The device as in claim 1, further comprising a protective layer which covers the loop portion and which prevents the arm portions from being prematurely pivoted downwardly from the intermediate portion.

7. The device as in claim 1, wherein the base portion is formed from a single block of generally rigid material, wherein the arm portions and intermediate portions are formed by longitudinal slots formed in the rigid material extending from a top surface to near a bottom surface of the single block of material, leaving unslotted areas of material defining a pair of hinges so that in use the arm positions can be pivoted on the pair of hinges.

8. A method of substantially uniformly and tightly crimping an intravascular stent onto a catheter assembly, comprising:

providing a device comprising a base portion having an intermediate portion and pivoting arm portions attached to the intermediate portion, and a loop portion for use in supporting a portion of the catheter assembly on which the stent may be positioned, the loop portion having a compressible and generally cylindrical opening portion which is substantially uniformly compressible radially inwardly upon the application of force thereto to substantially uniformly and tightly crimp the stent onto the catheter portion, the loop portion having end portions attached to the pivoting handle portions;

placing a portion of the catheter assembly, on which the stent is positioned, within the loop portion;

pivotally moving the arm portions relative to the intermediate portion to move the end portions of the loop portion in opposite directions thereby reducing the diameter of the generally cylindrical opening portion to apply compressive force to compress the stent radially inwardly, to substantially uniformly and tightly crimp the stent onto the catheter portion; and releasing the compressive force to enable radially outward expansion of the generally cylindrical opening portion to enable the stent and catheter portion to be withdrawn.

9. The method as in claim 8, wherein the loop portion comprises a sheet of flexible material, the end portions having a plurality of elongate straps extending from a first side edge of the sheet and a second side edge of the sheet, the sheet having apertures formed therethrough, wherein the elongate straps are threaded through the apertures formed in the sheet to establish the generally cylindrical loop opening portion, which loop opening is configured to constrict when the elongate straps and the second side edge of the sheet are pulled in opposite directions.

10. The method as in claim 8, wherein the device is covered with a removable protective layer to protect the loop portion and to prevent the arm portions from prematurely pivoting from the intermediate portion.

\* \* \* \* \*

UNITED STATES PATENT AND TRADEMARK OFFICE
CERTIFICATE OF CORRECTION

PATENT NO.  : 5,972,016
DATED       : Oct. 26, 1999
INVENTOR(S) : Stephen A. Morales It is certified that error appears in the above-identified patent and that said Letters Patent is hereby corrected as shown below:

Title page, under "FOREIGN PATENT DOCUMENTS", add the following:

```
--WO98/14120    4/1998    PCT.
  WO98/19633    5/1998    PCT--.
```

Signed and Sealed this

Twenty-third Day of May, 2000

Attest:

Q. TODD DICKINSON

*Attesting Officer*     *Director of Patents and Trademarks*